United States Patent [19]

Hlavka et al.

[11] 4,048,431

[45] Sept. 13, 1977

[54] ALKYLATED DERIVATIVES OF ANTIBIOTIC BM123γ

[75] Inventors: Joseph John Hlavka, Tuxedo; Panayota Bitha, Pomona, both of N.Y.

[73] Assignee: American Cyanamid Company, Stamford, Conn.

[21] Appl. No.: 630,564

[22] Filed: Nov. 10, 1975

Related U.S. Application Data

[63] Continuation-in-part of Ser. No. 612,975, Sept. 12, 1975, abandoned, which is a continuation-in-part of Ser. No. 529,862, Dec. 5, 1974, abandoned.

[51] Int. Cl.$^2$ .................. A61K 31/71; C07H 15/22
[52] U.S. Cl. ............................ 536/17; 195/31 R; 195/96; 424/181; 536/4
[58] Field of Search ............. 260/210 AB; 536/4, 17

[56] References Cited

U.S. PATENT DOCUMENTS

| | | | |
|---|---|---|---|
| 3,350,387 | 10/1967 | Vanderhaeghe | 260/210 AB |
| 3,784,541 | 1/1974 | Culbertson et al. | 260/210 AB |
| 3,978,041 | 8/1976 | Jaegge et al. | 536/4 |

FOREIGN PATENT DOCUMENTS

| | | | |
|---|---|---|---|
| 1,033,394 | 6/1966 | United Kingdom | 260/210 AB |

Primary Examiner—Johnnie R. Brown
Attorney, Agent, or Firm—Edward A. Conroy, Jr.

[57] ABSTRACT

This disclosure describes a novel series of potent antibacterial agents derived by reductive alkylation of antibiotic BM123γ with certain classes of aldehydes and ketones.

36 Claims, No Drawings

ALKYLATED DERIVATIVES OF ANTIBIOTIC BM123γ

CROSS REFERENCE TO RELATED APPLICATIONS

This application is a continuation-in-part of our co-pending application Ser. No. 612,975, filed Sept. 12, 1975, which in turn is a continuation-in-part of application Ser. No. 529,862, filed Dec. 5, 1974, both now abandoned.

BRIEF SUMMARY OF THE INVENTION

This invention relates to a novel group of antibiotics and, more particularly, is concerned with a novel series of potent antibacterial agents derived by reductive alkylation of antiobiotic BM123γ with an aldehyde or ketone of the following general formulae:

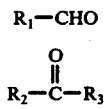

wherein $R_1$ is hydrogen, lower alkyl, halo substituted lower alkyl, lower alkenyl, phenyl, monosubstituted phenyl, phenyl lower alkyl, 2-furyl, methyl substituted 2-furyl, 2-thienyl, methyl substituted 2-thienyl, 2-pyrryl, methyl substituted 2-pyrryl, 2-pyridyl or 2-quinolyl; $R_2$ is lower alkyl, halo substituted lower alkyl or phenyl lower alkyl; $R_3$ is lower alkyl, halo substituted lower alkyl, lower alkenyl, lower cycloalkyl, phenyl, monosubstituted phenyl, phenyl lower alkyl or monosubstituted phenyl lower alkyl; and $R_2$ and $R_3$ taken together with the associated carbonyl group is cyclopentanone, mono-lower alkyl substituted cyclopentanone, di-lower alkyl substituted cyclopentanone, tri-lower alkyl substituted cyclopentanone, cyclohexanone, mono-lower alkyl substituted cyclohexanone, di-lower alkyl substituted cyclohexanone or tri-lower alkyl substituted cyclohexanone. Suitable lower alkyl and halo substituted lower alkyl groups contemplated by the present invention are those having up to six carbon atoms wherein halo is exemplified by chloro, bromo, and iodo such as methyl, ethyl, isopropyl, sec-butyl, n-amyl, dichloromethyl, 2-bromoethyl, 2,3-diiodopropyl, γ-chloropropyl, etc. Suitable lower alkenyl groups are those having up to four carbon atoms such as vinyl, allyl, propenyl, isopropenyl, 1-butenyl, 2-butenyl, 3-butenyl, isobutenyl, etc. Suitable lower cycloalkyl groups are cyclopenyl, cyclohexyl, and cycloheptyl. Suitable monosubstituted phenyl groups contemplated by the present invention are, for example, p-acetamidophenyl, m-nitrophenyl, m-mercaptophenyl, o-anisyl, p-anisyl, o-tolyl, p-tolyl, and the like whereas phenyl lower alkyl is exemplified by benzyl, α-phenylethyl, and β-phenylethyl. Suitable monosubstituted phenyl lower alkyl groups may be o, m, or p-chlorobenzyl, α-(p-aminophenyl)ethyl, β-(m-nitrophenyl)ethyl, etc. Suitable methyl substituted 2-furyl, 2-thienyl, and 2-pyrryl groups which may be employed are, for example, 5-methyl-2-furyl, 3,4-dimethyl-2-furyl, 4-methyl-2-thienyl, 3,5-dimethyl-2-thienyl, 5-methyl-2-pyrryl, 1,3,4-trimethyl-2-pyrryl, and the like.

The reductive alkylation process whereby the novel antibacterial agents of the present invention may be prepared is carried out as follows. Antibiotic BM123γ, BM123γ$_1$, or BM123γ$_2$ is dissolved in a suitable solvent such as water, methanol, methyl cellosolve, or mixtures thereof, an amount in excess of an equimolar amount of the desired aldehyde or ketone is then added followed by the addition of a reductive sufficiency of sodium cyanobrorohydride. The pH of the reaction mixture is maintained at 6.0–8.0 with dilute mineral acid during the course of the reaction. After one to 24 hours at ambient temperature (10°–35° C.), the reaction mixture is evaporated to dryness in vacuo and the residue is triturated with methanol and filtered. The filtrate is diluted with acetone and the solid product that precipitates is removed by filtration and dried in vacuo.

Aldehydes which may be so employed in the above process are, for example, acetaldehyde, propionaldehyde, butyraldehyde, isobutyraldehyde, crotonaldehyde, valeraldehyde, benzaldehyde, p-cyanobenzaldehyde, salicylaldehyde, cinnamaldehyde, trichloroacetaldehyde, etc. Ketones which may be so employed in the above process are, for example, acetone, 2-butanone, 1,3-dibromoacetone, chloroacetone, acetophenone, m-chloroacetophenone, p-bromoacetophenone, p-trifluoromethylacetophenone, m-nitroacetophenone, p-dimethylaminoacetophenone, etc.

The products are obtained from the reductive alkylation reaction mixtures by standard procedures such as precipitation, concentration, solvent extraction or combinations of these procedures. After isolation, the products may be purified by any of the generally known methods for purification. These include recrystallization from various solvents and mixed solvent systems, chromatographic techniques, and counter current distribution, all of which are usually employed for this purpose.

The novel antibacterial agents of the present invention are organic bases and thus are capable of forming acid-addition salts with a variety of organic and inorganic salt-forming reagents. Thus, acid-addition salts, formed by admixture of the antibacterial free base with up to three equivalents of an acid, suitably in a neutral solvent, are formed with such acids as sulfuric, phosphoric, hydrochloric, hydrobromic, sulfamic, citric, maleic, fumaric, tartaric, acetic, benzoic, gluconic, ascorbic, and related acids. The acid-addition salts of the antibacterial agents of the present invention are, in general, crystalline solids relatively soluble in water, methanol and ethanol but are relatively insoluble in non-polar organic solvents such as diethyl ether, benzene, toluene, and the like. For purposes of this invention, the antibacterial free bases are equivalent to their non-toxic acid addition salts.

DETAILED DESCRIPTION OF THE INVENTION

The antibiotics designated BM123β$_1$, BM123β$_2$, BM123γ$_1$ and BM123γ$_2$ are formed during the cultivation under controlled conditions of a new strain of an undetermined species of *Nocardia*. This new antibiotic producing strain was isolated from a garden soil sample collected at Oceola, Iowa, and is maintained in the culture collection of the Lederle Laboratories Division, American Cyanamid Company, Pearl River, N.Y. as Culture No. BM123. A viable culture of the new microorganism has been deposited with the Culture Collection Laboratory, Northern Utilization Research and Development Division, United States Department of Agriculture, Peoria, Illinois, and has been added to its permanent collection. It is freely available to the public in this depository under its accession No. NRRL 5646. Herein BM123β refers to a mixture in any proportion of BM123β₁ and BM123β₂, and BM123γ refers to a mixture in any proportion of BM123γ₁ and BM123γ₂.

The following is a general description of the microorganism *Nocardia sp.*, NRRL 5646, based on diagnostic characteristics observed. Observations were made of the cultural, physiological, and morphological features of the organism in accordance with the methods detailed by Shirling and Gottlieb, Internat. Journ, of Syst, Bacteriol. 16:213-240 (1966). The chemical composition of the culture was determined by the procedures given by Lechevalier et al., Advan. Appl. Microbiol. 14:47–72 (1971). The underscored descriptive colors and color chip designations are taken from Jacobson et al., Color Harmony Manual, 3rd ed. (1948), Container Corp. of America, Chicago, Illinois. Descriptive details are recorded in Tables I through V below.

Amount of Growth

Moderate on yeast extract, asparagine dextrose, Benedict's, Bennett's potato dextrose and Weinstein's agars; light on Hickey and Tresner's, tomato paste, oatmeal, and pablum agars and a trace of growth on inorganic salts-starch, Kuster's oatflake, Czapek's solution, and rice agars.

Aerial Mycelium

Aerial mycelium whitish when present; produced only on yeast extract, asparagine dextrose, Benedict's, Bennett's and potato dextrose agars.

Soluble Pigments

No soluble pigments produced.

Reverse Color

Colorless to yellowish shades.

Miscellaneous Physiological Reactions

No liquefaction of gelatin; nitrates reduced to nitrites in 7 days; melanoid pigments not formed on peptone-iron agar; no peptonization or curd formation in purple milk; NaCl tolerance in yeast extract agar ≧ 4% but ≦ 7%; optimal growth temperature 32° C. Carbon source utilization, according to the Pyridham and Gottlieb method [J. Bacteriol. 56:107-114 (1948)] as follows: Good utilization of glycerol, salicin, d-trehalose and dextrose; fair utilization of i-inositol; and poor to non-utilization of d-fructose, maltose, adonitol, 1-arabinose, lactose, d-mannitol, d-melibiose, d-raffinose, 1-rhamnose, sucrose and d-xylose.

Chemical Composition

The organism belongs to cell wall type IV, i.e., contains meso-2,6-diaminopimelic acid and has a type A whole-cell sugar pattern, i.e., contains arabinose and galactose. methylated whose cell extracts, when subjected to gas chromatography, showed fatty acid patterns similar to those produced by *Nocardia asteroides* ATCC 3308.

Micromorphology

Aerial mycelium arises from substrate mycelium as sparingly branched moderately long flexuous elements that commonly terminate in elongated primitive spirals. The flexuous elements are irregularly segmented into short elliptical to cyclindrical sections (spores) which disarticulate readily. The spiral terminal portions are less conspicuously segmented. Segments generally range 0.8–1.7 μm × 0.3–0.5 μm, averaging 0.4 μm × 1.2 μm.

Diagnosis

The morphological characteristics of Culture No. BM123 are difficult to observe and interpret because of the poor development of aerial mycelium on most media. Hence, considerable importance is attached, out of necessity, to the chemical analysis in determining the generic relationship of the organism. On the basis of the system proposed by Lechevalier et al., Culture No. BM123 contains meso-2,6-diaminopimelic acid in its whole cells and sugar analysis shows arabinose and galactose to be present. Therefore, the culture belongs to cell wall type IV. A comparison of the gas chromatography pattern of Culture No. BM123 with that of *Nocardia asteroides* ATCC 3308 showed the two to be remarkably similar. Other characteristics of Culture No. BM123 that are in keeping with the *Nocardia* concept, are its fragmenting aerial growth on some media and the total absence of aerial growth on most media. In view of the lack of adequate criteria for the characterization of *Nocardia* to the species level, no attempt has been made to make this determination. Therefore, Culture No. BM123 will be considered an undetermined species of *Nocardia* until such a diagnosis is feasible.

TABLE I

Cultural Characteristics of *Nocardia sp.* NRRL 5646

Incubation: 14 days — Temperature: 32° C.

| Medium | Amount of Growth | Aerial Mycelium And/Or Spores | Soluble Pigment | Reverse Color | Remarks |
|---|---|---|---|---|---|
| Yeast Extract Agar | Moderate | Aerial mycelium whitish, light | None | Mustard (3 ie) | Darkened areas in substrate mycelium. Coremia formed on surface mycelium |
| Hickey and Tresner's Agar | Light | No aerial mycelium | None | Colorless to Yellowish-green | Peripheral areas of colonies becoming olive-green |
| Asparagine dextrose Agar | Moderate | Trace of whitish aerial mycelium | None | Amber (3 lc) | Surface lightly wrinkled |
| Benedict's Agar | Moderate | Aerial mycelium whitish light | None | Nude Tan (4 gc) | Coremia abundantly formed on surface mycelium |
| Bennett's Agar | Moderate | Trace of whitish aerial mycelium | None | Camel (3 ie) | Surface lightly wrinkled |
| Inorganic Salts-starch Agar | Trace | No aerial mycelium | None | Colorless | |
| Kuster's Oatflake Agar | Trace | No aerial mycelium | None | Colorless | |
| Czapek's Solution Agar | Trace | No aerial mycelium | None | Colorless | |

TABLE I-continued
Cultural Characteristics of *Nocardia sp.* NRRL 5646

| | Incubation: 14 days | | | Temperature: 32° C. | |
|---|---|---|---|---|---|
| Medium | Amount of Growth | Aerial Mycelium And/Or Spores | Soluble Pigment | Reverse Color | Remarks |
| Potato dextrose Agar | Moderate | Aerial mycelium whitish, light | None | Camel (3 ie) | |
| Tomato Paste Oatmeal Agar | Light | No aerial mycelium | None | Colorless | |
| Pablum Agar | Light | No aerial mycelium | None | Colorless | |
| Rice Agar | Trace | No aerial mycelium | None | Colorless | |
| Weinstein's Agar | Moderate | No aerial mycelium | None | Colorless to yellowish | |

TABLE II
Micromorphology of *Nocardia sp.* NRRL 5646

| Medium | Aerial Mycelium and/or Sporiferous Structures |
|---|---|
| Yeast Extract Agar | Aerial mycelium arises from substrate mycelium as sparingly branced, flexous elements that commonly terminate in elongated primitive spirals. The flexuous elements are irregularly segmented into short sections (spores?) which disarticulate readily. The spiral terminal portions are less conspicuously segmented. Segments generally range 0.8–1.7 μm × 0.3–0.5 μm, averaging 0.4 μm × 1.2 μm |

TABLE III
Miscellaneous Physiological Reaction of *Nocardia sp.* NRRL 5646

| Medium | Incubation Period | Amount of Growth | Physiological Reaction |
|---|---|---|---|
| Gelatin | 7 days | Light | No liquefaction |
| Gelatin | 14 days | Good | No liquefaction |
| Organic Nitrate Broth | 7 days | Good | Nitrates reduced to nitrites |
| Organic Nitrate Broth | 14 days | Good | Nitrates reduced to nitriles |
| Peptone-iron Agar | 24–48 hours | Good | No melanin pigments reduced |
| Purple Milk | 7 days | Good | No peptonization or curd formation |
| Yeast extract Agar plus (4, 7, 10 and 13%) NaCl | 7 days | Moderate | NaCl tolerance $\geq 4\%$ but $\leq 7\%$ |

TABLE IV
Carbon Source Utilization Pattern of *Nocardia sp.* NRRL 5646

| Incubation: 10 days | Temperature: 32° C. |
|---|---|
| Carbon Source | Utilization* |
| Adonitol | 0 |
| 1-Arabinose | 0 |
| Glycerol | 3 |
| d-Fructose | 1 |
| i-Inositol | 2 |
| Lactose | 0 |
| d-Mannitol | 0 |
| Salicin | 2 |
| d-Melibiose | 0 |
| d-Raffinose | 0 |
| Rhamnose | 0 |
| Maltose | 1 |
| Sucrose | 0 |
| d-Trehalose | 3 |
| d-Xylose | 0 |
| Dextrose | 3 |
| Negative Control | 0 |

*3-Good Utilization
2-Fair Utilization
1-Poor Utilization
0-No Utilization

TABLE V
Chemical Composition of *Nocardia sp.* NRRL 5646

| Cell Wall Type | Major Constituents |
|---|---|
| Type IV | meso-DAP, arabinose, galactose |

The production of BM123β and BM123γ is not limited to this particular organism or to organisms fully answering the above growth and microscopic characteristics which are given for illustrative purposes only. In fact, mutants produced from this organism by various means such as exposure to X-radiation, ultra-violet radiation, nitrogen mustard, actinophages, and the like, may also be used. A viable culture of a typical such mutant strain has been deposited with the Culture Collection Laboratory, Northern Utilization Research and Development Division, United States Department of Agriculture, Peoria, Illinois, and has been added to its permanent collection under its accession number NRRL 8050. Although the cultural, physiological, and morphological features of NRRL 8050 are substantially the same as those of NRRL 5646, it produces enhanced amounts of BM123γ during aerobic fermentation. Also, NRRL 8050 varies from the parent NRRL 5646 as follows:

a. slower reduction of nitrates to nitrites; and
b. production of a rosewood tan mycelial pigment on Bennett's and yeast extract agars.

The novel antibacterial agents of the present invention are, in general, crystalline solids of relatively limited solubility in non-polar solvents such as diethyl ether and hexane, but considerably more soluble in solvents such as water and lower alkanols. Antibiotics BM123γ$_1$ and BM123γ$_2$ are structural isomers and may be represented by the following structural formulae:

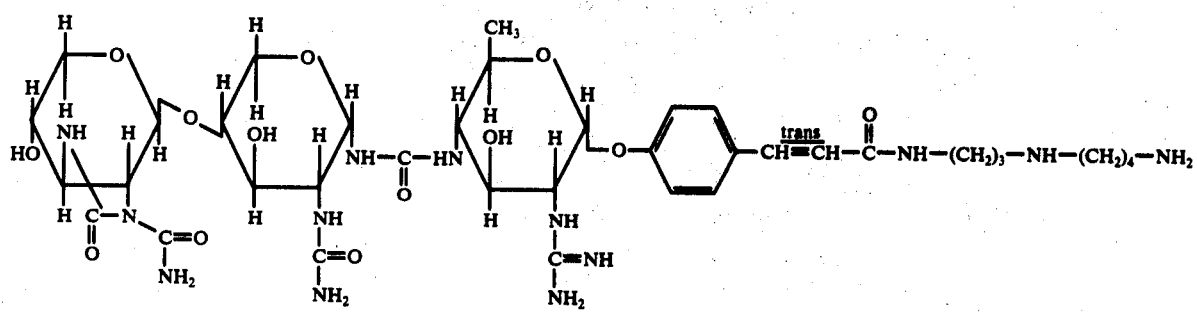

BM123γ₁

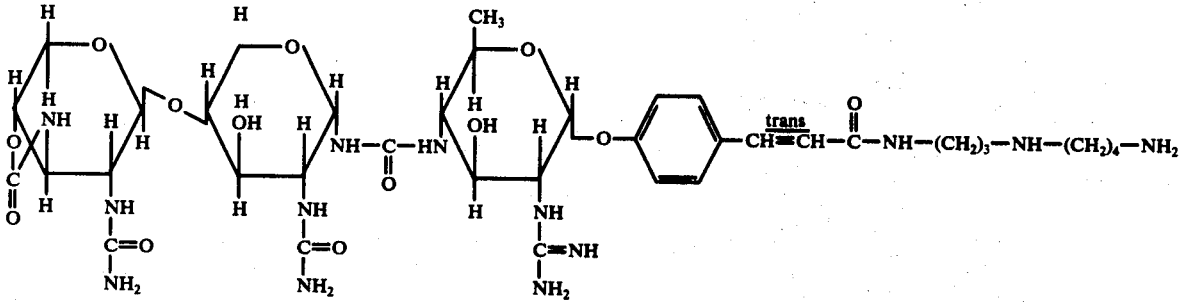

BM123γ₂

The reductive alkylation of BM123γ, BM123γ₁ or BM123γ₂ with ketones takes place on the spermadine side-chain to form derivatives of the formula:

and R₂ and R₃ are as hereinabove defined. The reductive alkylation of BM123γ, BM123γ₁ or BM123γ₂ with aldehydes takes place on the spermadine side-chain to form

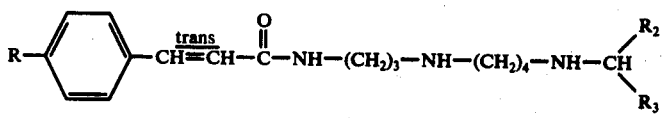

wherein R is a moiety of the formulae:

mono-, di-, and tri-substituted derivatives of the formulae:

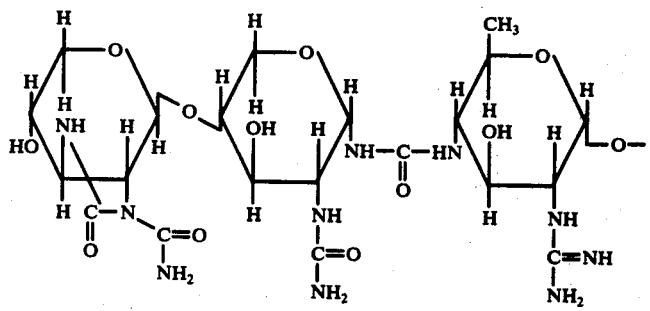

or

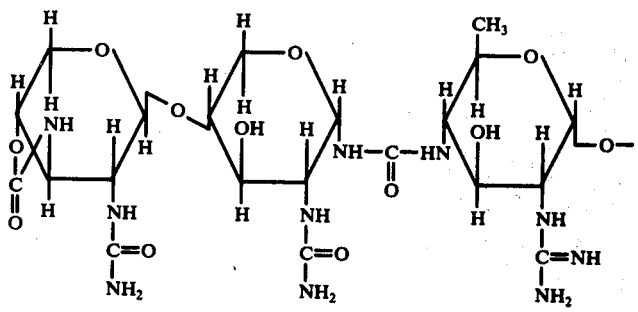

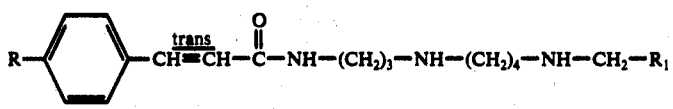

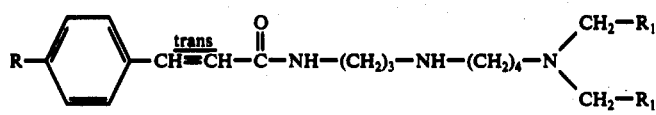

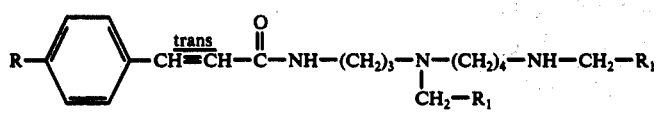

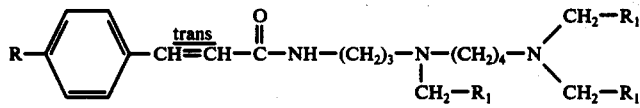

wherein R and $R_1$ are as hereinabove defined.

The usefulness of the alkylated derivatives of BM123γ is demonstrated by their ability to control systemic lethal infections in mice. These new substances show high in vivo antibacterial activity in mice against *Escherichia coli* US311 when administered by a single subcutaneous dose to groups of Carworth Farms CF-1 mice, weight about 20 gm., infected intraperitoneally with a lethal dose of this bacteria in a $10^{-3}$ trypticase soy broth TSP dilution of a 5 hour TSP blood culture. In Table VI below is set forth the in vivo activity of typical products of this invention (prepared from the indicated carbonyl reagents) against *Escherichia coli* US311 in mice. The activity is expressed in terms of the $ED_{50}$ or the dose in mg./kg. of body weight required to protect 50% of the mice against *E. coli*.

TABLE VI

| Carbonyl Reagent Employed | Derivative Name | $ED_{50}$ in mg./kg. of body weight |
|---|---|---|
| 1-dipropylamino-2-propanone | 1-methyl-2-(N,N-dipropylamino)-ethyl-BM123γ | 0.3 |
| 1-chloro-3-pentanone | 1-ethyl-3-chloropropyl-BM123γ | 0.12 |
| cyclooctanone | cyclooctyl-BM123γ | 0.18 |
| 4-methyl-2-pentanone | 1,3-dimethylbutyl-BM123γ | <0.12 |
| phenylacetone | 1-methyl-2-phenylethyl-BM123γ | 0.18 |
| trans-4-phenyl-3-buten-2-one | 1-methyl-3-phenylpropen(-2-)yl-BM123γ | 0.25 |
| 1-cyclohexyl-1-propanone | 1-cyclohexylpropyl-BM123γ | 0.37 |
| 6-methyl-5-hepten-2-one | 1,5-dimethylhexen(-4-)yl-BM123γ | 0.06 |
| 3-methyl-2-pentanone | 1,2-dimethylbutyl-BM123γ | 0.12 |
| 5-methyl-2-hexanone | 1,4-dimethylpentyl-BM123γ | 0.12 |
| 3-ethyl-2-pentanone | 1-methyl-2-ethylbutyl-BM123γ | 0.18 |
| 3,5-dimethyl-2-octanone | 1,2,4-trimethylheptyl-BM123γ | 0.37 |
| 3-octanone | 1-ethylhexyl-BM123γ | 0.18 |
| 3-methyl-2-hexanone | 1,2-dimethylpentyl-BM123γ | 0.18 |
| 3-indolylacetone | 1-methyl-2-(β-indolyl)ethyl-BM123γ | 0.12 |
| 2-pentanone | 1-methylbutyl-BM123γ | <0.12 |
| 2-butanone | 1-methylpropyl-BM123γ | <0.12 |
| 2-cyclopenten(-1-)yl-acetone | 1-methyl-2-cyclopenten(-2-)yl-ethyl-BM123γ | <0.12 |
| acetone | isopropyl-BM123γ | <0.12 |
| 3-decanone | 1-ethyloctyl-BM123γ | 0.25 |
| 3-undecanone | 1-ethylnonyl-BM123γ | 0.38 |
| o-acetoacetotoluidide | 1-methyl-2-o-[tolylcarbamoylethyl]-BM123γ | 0.25 |
| mesityl oxide | 1,3-dimethylbuten(-2-)yl-BM123γ | 0.3 |
| methoxyacetone | 1-methyl-2-methoxyethyl-BM123γ | 0.3 |
| cyclohexylacetone | 1-methyl-2-cyclohexylethyl-BM123γ | 0.18 |
| 4-(p-hydroxyphenyl)-2-butanone | 1-methyl-3-(4-hydroxyphenyl)ethyl-BM123γ | 0.3 |
| dimethyl(2-oxoheptyl)phosphonate | 1-[(dimethoxyphosphinyl)methyl]-hexyl-BM123γ | 0.3 |
| 4-methyl-2-hexanone | 1,3-dimethylpentyl-BM123γ | <0.12 |
| 2,2,4,4-tetramethylcyclopentanone | 2,2,4,4-tetramethylcyclopentyl-BM123γ | 0.75 |
| 2,4,4-trimethylcyclopentanone | 2,4,4-trimethylcyclopentyl-BM123γ | 0.3 |
| 2-cyclopentylcyclopentanone | 2-cyclopentylcyclopentyl-BM123γ | 0.37 |
| 2-(cyclo-1-hexenyl)cyclohexanone | 2-(1-cyclohexen)cyclohexyl-BM123γ | 0.19 |
| 3-tert-pentylcyclopentanone | 3-tert-pentylcyclopentyl-BM123γ | 0.5 |
| 2-cyclohexylcyclohexanone | 2-cyclohexylcyclohexyl-BM123γ | 0.75 |
| 2-ethylcyclohexanone | 2-ethylcyclohexyl-BM123γ | 0.19 |
| 3,3-dimethyl-2-butanone | 1,2,2-trimethylpropyl-BM123γ | <0.12 |
| 2-undecanone | 1-methyldecyl-BM123γ | >2 |
| tetrahydrothiopyran-4-one | 4-tetrahydrothiopyranyl-BM123γ | 0.38 |
| 3,5-dimethylcyclohexanone | 3,5-dimethylcyclohexyl-BM123γ | <0.12 |
| 2-tetradecanone | 1-methyltridecyl-BM123γ | 2.0 |
| 1-methoxy-1-buten-3-one | 1-methyl-3-methoxypropen(-2-)yl-BM123γ | >2.0 |
| 4-hydroxy-3-methyl-2-butanone | 1,2-dimethyl-3-hydroxypropyl-BM123γ | 0.12 |
| menthone | 3-methyl-6-isopropylcyclohexyl-BM123γ | 0.38 |

TABLE VI-continued

| Carbonyl Reagent Employed | Derivative Name | $ED_{50}$ in mg./kg. of body weight |
|---|---|---|
| cyclononanone | cyclononyl-BM123γ | 0.18 |
| 1-methyl-2-decalone | decahydro-1-methyl-2-naphthyl-BM123γ | 0.25 |
| isophorone | 3,3-dimethylcyclohexen(-4-)yl-BM123γ | 0.37 |
| 3-methyl-2-decalone | decahydro-3-methyl-2-naphthyl-BM123γ | 0.37 |
| 1-(3,4-dimethoxyphenyl)-2-butanone | 2-ethyl-2-(3,4-dimethoxyphenyl)ethyl-BM123γ | 1.0 |
| 1-diethylamino-3-butanone | 1-methyl-3-(N,N-diethylamino)propyl-BM123γ | 0.18 |
| ethyl 2-chloroacetoacetate | 1-methyl-2-chloro-2-carbethoxyethyl--BM123γ | 1.5 |
| 3-hydroxy-3-methyl-2-butanone | 1,2,2-dimethylhydroxypropyl-BM123γ | 0.18 |
| 3-pentanone | 1-ethylpropyl-BM123γ | 0.12 |
| 3-methyl-2-butanone | 1,2-dimethylpropyl-BM123γ | 0.19 |
| p-chlorophenylacetone | 1-methyl-2-(4-chlorophenyl)ethyl-BM123γ | 0.25 |
| N-(tert-butyl)acetoacetamide | 2-(tert-butylcarbamoyl)-1-methyl-ethyl-BM123γ | 0.38 |
| 1,1-dimethoxyacetone | 1-methyl-2,2-dimethoxyethyl-BM123γ | 0.5 |
| 4-heptanone | 1-propylbutyl-BM123γ | 0.25 |
| 3-methoxyphenylacetone | 1-methyl-2-(3-methoxyphenyl)ethyl-BM123γ | 0.30 |
| 1,3-acetonedicarboxylic acid | (2-carboxy-1-carboxymethyl)ethyl-BM123γ | 0.5 |
| 2-phenylcyclohexanone | 2-phenylcyclohexyl-BM123γ | 0.38 |
| phenoxy-2-propanone | 1-methyl-2-phenoxyethyl-BM123γ | 0.3 |
| 3-butyn-2-one | 1-methyl-butyn(-2-)yl-BM123γ | <2.0 |
| dimethylaminoacetone | 1-methyl-2-(N,N-dimethylamino)propyl-BM123γ | 1.5 |
| 5-diethylamino-2-pentanone | 1-methyl-4-(N,N-diethylamino)butyl-BM123γ | 0.5 |
| 2-cyclohexen-1-one | 2-cyclohexenyl-BM123γ | 0.25 |
| cyclopropylmethylketone | 1-cyclopropylethyl-BM123γ | 0.25 |
| 4,4-dimethoxy-2-butanone | 1-methyl-3,3-dimethoxypropyl-BM123γ | 0.75 |
| 1,3-dimethylacetonedicarboxylate | 1-carbomethoxy-2-carbomethoxyethyl-BM123γ | 0.75 |
| 2-methoxyphenylacetone | 1-methyl-2-(2-methoxyphenyl)ethyl-BM123γ | 0.7 |
| acetylacetone | 1-methyl-2-acetylethyl-BM123γ | 1.5 |
| cyclobutanone | cyclobutyl-BM123γ | 0.38 |
| p-chlorophenylacetone | 1-methyl-2-(4-chlorophenyl)ethyl-BM123γ | 0.25 |
| 2-octanone | 1-methylheptyl-BM123γ | 0.38 |
| 4-phenyl-2-butanone | 1-methyl-3-phenylpropyl-BM123γ | 0.38 |
| 5-chloro-2-pentanone | 1-methyl-4-chlorobutyl-BM123γ | 0.37 |
| o-chlorophenylacetone | 1-methyl-2-(2-chlorophenyl)ethyl-BM123γ | 0.37 |
| m-chlorophenylacetone | 1-methyl-2-(3-chlorophenyl)ethyl-BM123γ | 0.38 |
| 5-hexene-2-one | 1-methyl-penten(-4-)yl-BM123γ | 0.38 |
| cyclohexanone | cyclohexyl-BM123γ | 0.75 |
| 2-hexanone | 1-methylpentyl-BM123γ | 0.38 |
| 2-heptanone | 1-methylhexyl-BM123γ | 0.38 |
| cycloheptanone | cycloheptyl-BM123γ | 0.3 |
| cyclopentanone | cyclopentyl-BM123γ | 0.25 |
| 4,4-dimethyl-2-pentanone | 1,3,3-trimethylbutyl-BM123γ | 0.18 |
| 2-acetamido-3-butanone | 2-acetamido-1-methylpropyl-BM123γ | 0.50 |
| 2,6-dimethyl-3-heptanone | 1-isopropyl-4-methylpentyl-BM123γ | 0.39 |
| 4-octanone | 1-propylpentyl-BM123γ | 0.39 |
| 3-acetylpyridine | 1-(3-pyridyl)ethyl-BM123γ | 0.75 |
| 3-heptanone | 1-ethylpentyl-BM123γ | 0.25 |
| ethyl butyrylacetate | 1-(carbethoxymethyl)butyl-BM123γ | 0.75 |
| 1-benzyl-4-piperidone | 1-benzyl-4-piperidyl-BM123γ | 0.18 |
| 1-methyl-4-piperidone | 1-methyl-4-piperidyl-BM123γ | 0.75 |
| 3-methylcyclopentanone | 3-methylcyclopentyl-BM123γ | 0.25 |
| 3,3-dimethyl-2-butanone | 1-methyl-2,2-dimethylpropyl-BM123γ | 0.18 |
| 2-acetyl-5-norbornene | 1-[5-norbornene(2)]ethyl-BM123γ | <0.12 |
| bicyclo[3.2.1]octan-2-one | bicyclo[3.2.1]octanyl-2-BM123γ | <0.25 |
| 3-quinuclidinone | 3-quinuclidinyl-BM123γ | 0.39 |
| 5-methoxyl-2-tetralone | 5-methoxyl-2-tetralyl-BM123γ | 0.18 |
| 4-methyl-2-heptanone | 1,3-dimethylhexyl-BM123γ | 0.5 |
| 3,4-dimethyl-2-hexanone | 1,2,3-trimethylpentyl-BM123γ | 0.39 |
| 1,3,3-trimethylcyclopentanone | 1,3,3-trimethylcyclopentyl-BM123γ | 0.37 |
| acetylcyclopentanone | 1-cyclopentylethyl-BM123γ | 0.18 |
| 5-hexen-2-one | 1-methyl-hexen-4-yl-BM123γ | 0.18 |
| 2-methylcyclopentanone | 2-methylcyclopentyl-BM123γ | 0.25 |
| 2,4-dimethylcyclopentanone | 2,4-dimethylcyclopentyl-BM123γ | 0.18 |
| 2-ethylcyclopentanone | 2-ethylcyclopentyl-BM123γ | 0.12 |
| 2-adamantone | adamantyl-2-BM123γ | 0.25 |
| 3-hexanone | 1-ethylbutyl-BM123γ | 0.39 |
| ethyl 2-methylacetoacetate | 1-methyl-2-carboethoxypropyl-BM123γ | 0.18 |
| norbornanone | norbornyl-BM123γ | 0.18 |
| 5-hexene-2-one | 1-methyl-5-pentenyl-BM123γ | 0.18 |
| 3-hydroxy-2-butenone | 1-methyl-2-hydroxypropyl-BM123γ | 0.37 |
| 4-hydroxy-3-methyl-2-butanone | 1-methyl-2-(3-hydroxy-2-methylpropyl)-BM123γ | 0.18 |
| 2-nonanone | 1-methyloctyl-BM123γ | 0.37 |
| 5-hydroxy-2-pentanone | 1-methyl-4-hydroxybutyl-BM123γ | 0.18 |
| 2-decanone | 1-methylnonyl-BM123γ | 0.18 |
| 4-t-butylcyclohexanone | 4-t-butylcyclohexyl-BM123γ | 0.12 |
| 2-ethylidenecyclohexanone | 2-ethylidenecyclohexyl-BM123γ | 0.12 |
| phenylacetaldehyde | 2-phenylethyl-BM123γ | 0.18 |
| p-methoxyphenylacetaldehyde | 2-(p-methoxyphenyl)ethyl-BM123γ | 0.18 |

TABLE VI-continued

| Carbonyl Reagent Employed | Derivative Name | ED$_{50}$ in mg./kg. of body weight |
|---|---|---|
| 2-ethylhexanal | 2-ethylhexyl-BM123γ | 0.37 |
| 2,2-dimethylbutanal | 2,2-dimethylbutyl-BM123γ | 0.12 |
| 2,2-dimethylpropanal | 2,2-dimethylpropyl-BM123γ | 0.18 |
| 2-ethyl-2-butenal | 2-ethyl-2-butenyl-BM123γ | 0.18 |
| trans-2-methyl-2-butenal | trans-2-methyl-2-butenyl-BM123γ | 0.18 |
| 1-methylcyclo-3-hexenylmethanal | (1-methylcyclo-3-hexenyl)methyl-BM123γ | 0.18 |
| trans-2-methyl-2-pentenal | trans-2-methyl-2-pentenyl-BM123γ | 0.18 |
| formaldehyde | methyl-BM123γ | 0.12 |
| acetaldehyde | ethyl-BM123γ | 0.38 |

Fermentation Process Selected to Produce Primarily BM123β and BM123γ.

Cultivation of *Nocardia sp.* NRRL 8050 may be carried out in a wide variety of liquid culture media. Media which are useful for the production of the antibiotics include an assimilable source of carbon such as starch, sugar, molasses, glycerol, etc.; an assimilable source of nitrogen such as protein, protein hydrolyzate, polypeptides, amino acids, corn steep liquor, etc.; and inorganic anions and cations, such as potassium, magnesium, calcium, ammonium, sulfate, carbonate, phosphate, chloride, etc. Trace elements such as boron, molybdenum, copper, etc.; are supplied as impurities of other constituents of the media. Aeration in tanks and bottles is provided by forcing sterile air through or onto the surface of the fermenting medium. Further agitation in tanks is provided by a mechanical impeller. An antifoaming agent, such as Hodag® FD82 may be added as needed.

Inoculum Preparation for BM123β and BM123γ

Primary shaker flask inoculum of *Nocardia sp.* NRRL 8050 is prepared by inoculating 100 milliliters of sterile liquid medium in 500 milliliter flasks with scrapings or washings of spores from an agar slant of the culture. The following medium is ordinarily used:

| | |
|---|---|
| Bacto-tryptone | 5 gm. |
| Yeast extract | 5 gm. |
| Beef extract | 3 gm. |
| Glucose | 10 gm. |
| Water to | 1000 ml. |

The flasks were incubated at a temperature from 25°-29° C., preferably 28° C. and agitated vigorously on a rotary shaker for 30 to 48 hours. The inocula are then transferred into sterile screw cap culture tubes and stored at below 0° F. This bank of vegetative inoculum is used instead of slant scrapings for inoculation of additional shaker flasks in preparation of this first stage of inoculum.

These first stage flask inocula are used to seed 12 liter batches of the same medium in 20 liter glass fermentors. The inoculum mash is aerated with sterile air while growth is continued for 30 to 48 hours.

The 12 liter batches of second stage inocula are used to seed tank fermentors containing 300 liters of the following sterile liquid medium to produce the thrid and final stage of inoculum:

| | |
|---|---|
| Meat solubles | 15 gm. |
| Ammonium sulfate | 3 gm. |
| Potassium phosphate, dibasic | 3 gm. |
| Calcium carbonate | 1 gm. |
| Magnesium sulfate heptahydrate | 1.5 gm. |
| Glucose | 10 gm. |
| Water to | 1000 ml. |
| The glucose is sterilized separately. | |

The third stage inoculum is aerated at 0.4 to 0.8 liters of sterile air per liter of broth per minute, and the fermenting mixture is agitated by an impeller driven at 150-300 revolutions per minute. The temperature is maintained at 25°-29° C., usually 28° C. The growth is continued for 48 to 72 hours, at which time the inoculum is used to seed a 3000 liter tank fermentation.

Tank Fermentation for BM123β and BM123γ

For the production of BM123β and BM123γ in tank fermentors, the following fermentation medium is preferably used:

| | |
|---|---|
| Meat solubles | 30 gm. |
| Ammonium sulfate | 6 gm. |
| Potassium phosphate, dibasic | 6 gm. |
| Calcium carbonate | 2 gm. |
| Magnesium sulfate heptahydrate | 3 gm. |
| Glucose | 20 gm. |
| Water to | 1000 ml. |
| The glucose is sterilized separately. | |

Each tank is inoculated with 5 to 10% of third stage inoculum made as described under inoculum preparation. The fermenting mash is maintained at a temperature of 25°-28° C. usually 26° C. The mash is aerated with sterile air at a rate of 0.3-0.5 liters of sterile air per liter of mash per minute and agitated by an impeller driven at 70 to 100 revolutions per minute. The fermentation is allowed to continue from 65-90 hours and the mash is harvested.

The invention will be described in greater detail in conjunction with the following specific examples.

EXAMPLE 1

Inoculum preparation for BM123β and BM123γ

A typical medium used to grow the first and second stages of inoculum was prepared according to the following formula:

| | |
|---|---|
| Bacto-tryptone | 5 gm. |
| Yeast extract | 5 gm. |
| Beef extract | 3 gm. |
| Glucose | 10 gm. |
| Water to | 1000 ml. |

Two 500 milliliter flasks each containing 100 milliliters of the above sterile medium were inoculated with 5 milliliters each of a frozen vegetative inoculum from *Nocardia sp.* NRRL 8050. The flasks were placed on a rotary shaker and agitated vigorously for 48 hours at 28° C. The resulting flask inoculum was transferred to a 5 gallon glass fermentor containing 12 liters of the above sterile medium. The mash was aerated with sterile air while growth was carried out for about 48 hours, after which the contents were used to seed a 100 gallon tank fermentor containing 300 liters of the following sterile liquid medium:

| | |
|---|---|
| Meat solubles | 15 gm. |
| Ammonium sulfate | 3 gm. |
| Potassium phosphate, dibasic | 3 gm. |
| Calcium carbonate | 1 gm. |
| Magnesium sulfate heptahydrate | 1.5 gm. |
| Glucose | 10 gm. |
| Water to | 1000 ml. |
| The glucose is sterilized separately. | |

The third stage of inoculum mash was aerated with sterile air sparged into the fermentor at 0.4 liters of air per liter of mash per minute. Agitation was supplied by a driven impeller at 240 revolutions per minute. The mash was maintained at 28° C. and Hodag® FD82 was used as a defoaming agent. After 48 hours of growing time the inoculum mash was used to seed a 3000 liter fermentation.

EXAMPLE 2

Fermentation Employing Nocardia sp. NRRL 8050 and Medium Favoring the Production of BM123β and BM123γ

A fermentation medium was prepared according to the following formula:

| | |
|---|---|
| Meat solubles | 30 gm. |
| Ammonium sulfate | 6 gm. |
| Potassium phosphate, dibasic | 6 gm. |
| Calcium carbonate | 2 gm. |
| Magnesium sulfate heptahydrate | 3 gm. |
| Glucose | 20 gm. |
| Water to | 1000 ml. |
| The glucose is sterilized separately. | |

The fermentation medium was sterilized at 120° C. with steam at 20 pounds pressure for 60 minutes. The pH of the medium after sterilization was 6.9. Three thousand liters of sterile medium in a 4000 liter tank fermentor was inoculated with 300 liters of inoculum such as described in Example 1, and the fermentation was carried out at 26° C. using Hodag® FD82 as a defoaming agent. Aeration was supplied at the rate of 0.35 liter of sterile air per liter of mash per minute. The mash was agitated by an impeller driven at 70-72 revolutions per minute. At the end of 67 hours of fermentation time the mash was harvested.

EXAMPLE 3

Isolation of BM123β and BM128γ

A 3000 liter portion of fermentation mash prepared as described in Example 2, pH 4.3, was adjusted to pH 7.0 with sodium hydroxide and filtered using 5% diatomaceous earth as a filter aid. The cake was washed with about 100 liters of water and discarded. The combined filtrate and wash was pumped upward through three parallel 8¼ inches × 48 inches stainless steel columns each containing 15 liters of CM Sephadex® C-25 [Na+] resin (a cross-linked dextran-epichlorohydrin cation exchange gel available from Pharmacia Fine Chemicals, Inc.). The charged columns were washed with a total of about 390 liters of water and then developed with 200 liters of 1% aqueous sodium chloride followed by 560 liters of 5% aqueous sodium chloride. The 5% aqueous sodium chloride eluate was clarified by filtration through diatomaceous earth and the clarified filtrate passed through a 9 inches × 60 inches glass column containing 25 liters off granular Darco® G-60 (20-40 mesh) (a granular activated carbon available from Atlas Chemical Industries, Inc.). The charged column was washed with 120 liters of water and then developed with 120 liters of 15% aqueous methanol followed by 340 liters of 50% aqueous methanol and then 120 liters of 50% aqueous acetone. The 15% aqueous methanol eluate was concentrated in vacuo to about 7 liters of an aqueous phase and the pH adjusted from 4.5 to 6.0 with Amberlite® IR-45 (OH−) resin (a weakly basic polystyrene-polyamine type anion exchange resin). The resin was removed by filtration and the filtrate was concentrated in vacuo to about 1 liter and then lyophilized to give 38 grams of material consisting primarily of BM123β along with a small amount of BM123γ (primarily BM123γ$_2$). The 50% aqueous methanol eluate was adjusted from pH 4.65 to 6.0 with Amberlite® IR-45 (OH−) resin. The resin was removed by filtration and the filtrate was concentrated in vacuo to about 6.3 liters and then lyophylized to give 213 grams of material consisting primarily of BM123γ. The 50% aqueous acetone eluate was adjusted from pH 4.0 to 6.0 with Amberlite® IR-45 (OH−) resin. The resin was removed by filtration and the filtrate was concentrated in vacuo to about 1.5 liters and then lyophylized to give 56 grams of impure BM123γ.

EXAMPLE 4

Further Purification of BM123γ

A slurry of CM Sephadex® C-25 [NH$_4$+] in 2% aqueous ammonium chloride was poured into a 2.6 centimeter diameter glass column to a resin height of approximately 62 centimeters. The excess 2% aqueous ammonium chloride was drained away and a 5.0 gram sample of BM123γ prepared as described in Example 3 was dissolved in about 10 milliliters of 2% aqueous ammonium chloride and applied to the column. The column was then eluted with a gradient between 6 liters each of 2% and 4% aqueous ammonium chloride. Fractions of about 75 milliliters each were collected automatically every 15 minutes. Antibiotic BM123γ was located by monitoring the column effluent in the ultraviolet and by bioautography of dipped paper disks on large agar plates seeded with *Klebsiella pneumoniae* strain AD. The majority of BM123γ was located between fractions 71–107 inclusive.

One hundred thirty milliliters of granular Darco® G-60 (20-40 mesh) was suspended in water, transferred to a glass column, allowed to settle and the excess water was allowed to drain away. Fractions 84–96 inclusive from the above CM Sephadex chromatography were combined and passed through the granular carbon column. The charged column was washed with 600 milliliters of water and then developed with 1 liter of 50% aqueous acetone. The eluates, both of which contained BM123β, were concentrated to aqueous phases in vacuo and lyophilized to give a total of 886 milligrams of BM123γ as the hydrochloride salt. A microanalytical sample was obtained by subjecting the above material to a repeat of the above process.

Antibiotic BM123γ does not possess a definite melting point, but gradual decomposition starts in the vicinity of 200° C. Microanalysis of a sample equilibrated for 25 hours in a 72° F. atmosphere containing 23% relative humidity gave C, 39.44%; H, 6.10%; N, 16.19%; Cl(ionic), 11.54%; loss on drying, 8.19%. In water BM123γ gave a U.V. absorption maximum at 286 nm with $E_{1cm}^{1\%}$ = 250. The position of this maximum did not change with pH. BM123γ had a specific rotation of $[\alpha]_D^{25°} +71°$ (C = 0.97 in water).

Antibiotic BM123γ exhibited characteristic absorption in the infrared region of the spectrum at the following wavelengths: 770, 830, 870, 930, 980, 1035, 1105, 1175, 1225, 1300, 1340, 1370, 1460, 1510, 1555, 1605, 1660, 1740, 2950 and 3350 cm$^{-1}$. A standard infrared absorption spectrum of BM123γ prepared in a KBr pellet is shown in FIG. 1 of the accompanying drawings.

EXAMPLE 5

Isolation of BM123γ$_1$

A slurry of CM Sephadex® C-25 [Na+] in 2% aqueous sodium chloride was poured into a 2.6 centimeter diameter glass column to a resin heigh of approximately 70 centimeters. The excess 2% aqueous sodium chloride was drained away and 4.11 gram of a sample containing primarily BM123γ$_1$ along with some BM123γ$_2$ and other impurities, prepared as described in Example 3, was dissolved in about 10 milliliters of 2% aqueous sodium chloride and applied to the column. The column was then eluted with a gradient between 4 liters each of 2% and 4% aqueous sodium chloride. Fractions of about 75 milliliters each were collected automatically every 15 minutes. Antibiotic BM123γ was located by monitoring the column effluent in the ultraviolet and by bioautography of dipped paper disks on large agar plates seeded with *Klebsiella pneumoniae* strain AD. The majority of BM123γ was located between fractions 64–90 inclusive; the initial fractions (64–80) contained a mixture of BM123γ$_1$ and BM123γ$_2$ whereas the later fractions (81–90) contained essentially pure BM123γ$_1$.

One hundred milliliters of granular Darco® G-60 (20–40 mesh) was suspended in water, transferred to a glass columm, allowed to settle and the excess water was allowed to drain away. Fractions 81-90 inclusive from the above CM Sephadex chromatography were combined and passed through the granular carbon column. The charged column was washed with 500 milliliters of water and then developed with 500 milliliters of 10% aqueous methanol followed by 1 liter of 50% aqueous methanol. The 50% aqueous methanol eluate, which contained the majority of BM123γ$_1$, was adjusted from pH 5.9 to 6.0 with Amberlite® IR-45(OH$^{-1}$) resin. The resin was removed by filtration and the filtrate was concentrated in vacuo to an aqueous phase and lyophilized to give 294 milligrams of white amorphous BM123γ$_1$ as the hydrochloride salt.

Antibiotic BM123γ$_1$ does not possess a definite melting point, but gradual decomposition starts in the vicinity of 200° C. Microanalysis of a sample equilibrated for 24 hours in a 70° F. atmosphere containing 60% relative humidity gave C, 37.84%; H, 5.73%; N, 15.58%; Cl(ionic), 10.01%, loss on drying 10.45%. In methanol BM123γ$_1$ gave a U.V. absorption maximum at 286 nm with $E_{1cm}^{1\%} = 225$. The position of this maximum did not change with pH. BM123γ$_1$ had a specific rotation of +55° (C=0.803 in water).

Antibiotic BM123γ$_1$ exhibited characteristic absorption in the infrared region of the spectrum at the following wavelengths: 770, 830, 870, 930, 980, 1045, 1080, 1110, 1125, 1175, 1225, 1305, 1345, 1380, 1465, 1515, 1560, 1605, 1660, 1730, 2950 and 3350 cm$^{-1}$. A standard infrared absorption spectrum of BM123γ$_1$ prepared in a KBr pellet is shown in FIG. 2 of the accompanying drawings. A standard proton magnetic resonance spectrum of BM123γ$_1$ determined on a D$_2$O solution in a 100 megacycle spectrometer is shown in FIG. 4 of the accompanying drawings.

EXAMPLE 6

Isolation of BM123γ$_2$

A 25 gram sample containing primarily BM123γ$_2$ and BM123β, prepared as described in Example 3, was dissolved in about 120 milliliters of 2% aqueous sodium chloride and applied to a column containing 1800 ml. of CM Sephadex® C-25 [Na+] in 2% aqueous sodium chloride. The column was then eluted with a gradient between 20 liters each of 2% and 4% aqueous sodium chloride. The initial 12 liters of eluate was collected in a large bottle and discarded. Thereafter fractions of about 800 milliliters each were collected automatically every 40 minutes. Antiobiotic BM123γ was located by monitoring the column fractions in the ultraviolet. The majority of BM123γ was located between fractions 7–19 inclusive; the initial fractions (7–15) contained essentially pure BM123γ$_2$ and the later fractions (16–18) contained a mixture of BM123γ$_1$ and BM123γ$_2$.

Six hundred milliliters of granular Darco® G-60 (20–40 mesh) was suspended in water, transferred to a glass column, allowed to settle and the excess water was allowed to drain away. Fractions 7–15 inclusive from the above CM Sephadex chromatography were combined and passed through the granular carbon column. The charged column was washed with 3 liters of water and then developed with 3 liters of 10% aqueous methanol followed by 6 liters of 50% aqueous methanol. The 10% aqueous methanol eluate was adjusted from pH 5.8 to 6.0 with Amberlite® IR 45 (OH$^-$) resin. The resin was removed by filtration and the filtrate was concentrated in vacuo to an aqueous phase and lyophilized to give 595 milligrams of white amorphous BM123γ$_2$ as the hydrochloride salt. The 50% aqueous methanol eluate was adjusted from pH 4.6 to 6.1 with Amberlite® IR 45 (OH$^-$) resin. The resin was removed by filtration and the filtrate was concentrated in vacuo to an aqueous phase and lyophilized to give 3.645 grams of slightly less pure white amorphous BM123γ$_2$ as the hydrochloride salt.

Antibiotic BM123γ$_2$ does not possess a definite melting point, but gradual decomposition starts in the vicinity of 200° C. Microanalysis of a sample equilibrated for 24 hours in a 70° F. atmosphere containing 60% relative humidity gave C, 36.14%; H, 5.67%, N, 15.1%; Cl(ionic), 11.11%; loss on drying 10.87%. In methanol BM123γ$_2$ gave a U.V. absorption maximum at 286 nm with $E_{1cm}^{1\%} = 220$. The position of this maximum did not change with pH. BM123γ$_2$ had a specific rotation of +60° (C=0.851 in water).

Antibiotic BM123γ$_2$ exhibited characteristic absorption in the infrared region of the spectrum at the following wavelengths: 770, 830, 870, 950, 1035, 1110, 1175, 1225, 1285, 1345, 1380, 1470, 1515, 1560, 1605, 1660, 1755, 2950 and 3350 cm$^{-1}$. A standard infrared absorption spectrum of BM123γ$_2$ prepared in a KBr pellet is shown in FIG. 3 of the accompanying drawings. A standard proton magnetic resonance spectrum of BM123γ$_2$ determined on a D$_2$O solution in a 100 megacycle spectrometer is shown in FIG. 5 of the accompanying drawings.

EXAMPLE 7

Paper Partition and Thin Layer Chromatography of BM123β and BM123γ the BM123 antibiotics can be distinguished by paper chromatography. For this purpose Whatman No. 1 strips were spotted with a water or methanol solution of the substances and equilibrated for 1 to 2 hours in the presence of both upper and lower phases. The strips were developed overnight with the lower (organic) phase obtained from mixing 90% phenol:m-cresol:acetic acid:pyridine:water (100:25:4:4:75 by volume). The developed strips were removed from the chromatographic chamber, air dried for 1 to 2 hours, washed with ether to remove residual phenol and bioautographed on large agar plates seeded with Klebsiella peunmoniae strain AD. Representative Rf values are listed in Table VII below:

TABLE VII

| Component | RF |
|---|---|
| BM123γ | 0.85 |
| BM123β | 0.50, 0.70 |

The β component was a mixture of two antibiotics using this system. BM123β was composed of a major antibiotic (Rf = 0.50) called BM123β$_1$ and a minor antibiotic (Rf = 0.70) called BM123β$_2$.

The BM123 antibiotics can also be distinguished by thin layer chromatography. For this purpose pre-coated Cellulose F® plates (0.10 millimeters thick), a form of thick layer cellulose supplied by EM Laboratories Inc., Elmsford, N.Y. were spotted with a water solution of the substance to be chromatographed (about 20–40 micrograms per spot). The plates were developed overnight with the solvent obtained by mixing 1-butanol:-water:pyridine:acetic acid (15:12:10:1 by volume). The developed plates were removed from the chromatographic chamber and air dried for about 1 hour. The antibiotics were detected by using either standard ninhydrin or Sakaguchi spray reagents. Representative Rf values are listed in Table VIII below:

TABLE VIII

| Component | Rf |
|---|---|
| BM123γ | 0.17, 0.23 |
| BM123β | 0.08, 0.14 |

Both BM123β and γ were a mixture of two components using this system. BM123β was composed of a major component (Rf = 0.08) which was BM123β$_1$ and a minor component (Rf = 0.14) which was BM123β$_2$. The less polar component of BM123γ (Rf = 0.23) was BM123γ$_1$ and the more polar component (Rf = 0.17) was BM123γ$_2$.

EXAMPLE 8

General Procedure for Reductive Alkylation of Antibiotic BM123γ

To a stirred solution of 100 mg. of antibiotic BM123γ in 20 ml. of methanol is added 5 ml. (or 5 g.) of the appropriate aldehyde or ketone and 100 mg. of sodium cyanoborohydride. The pH of the resulting solution is maintained at about 7.0 with 0.1N methanolic hydrogen chloride over a 3 to 24 hour period. The reaction is monitored by thin layer chromatography to the disappearance of the BM123γ. The reaction mixture is then filtered and the filtrate is evaporated to dryness. The residue is triturated with 3 ml. of methanol and filtered. The filtrate is diluted with 50 ml. of acetone and the precipitate which forms is removed by filtration and dried. The methanol solvent may be replaced by 20 ml. of water wherever the starting aldehyde or ketone is water soluble.

EXAMPLE 9

Preparation of methyl-BM123γ

To a solution of 1.0 g. of BM123γ and 2.5 ml. of a 37% aqueous formaldehyde solution in 50 ml. of water was added, portionwise, 400 mg. of sodium cyanoborohydride. The pH of the reaction mixture was maintained at 7.0 with 1N hydrochloric acid during this addition. The reaction mixture was stirred an additional ten minutes at room temperature and then evaporated to dryness to vacuo. The residue was triturated with 20 ml. of methanol, filtered and the filtrate diluted with 250 ml. of acetone. The product which precipitated was removed by filtration and dried; yield, 667 mg.

EXAMPLE 10

Preparation of isopropyl-BM123γ

To a solution of 200 mg. of BM123γ in 30 ml. of methanol was added 5 ml. of acetone. To this solution was added 139 mg. of sodium cyanoborohydride and the reaction mixture was stirred at room temperature for 30 minutes. During this time the pH of the reaction mixture was maintained between 7.4 and 7.8 by the addition of 0.1N methanolic hydrogen chloride. The small amount of precipitate which had formed was removed by filtration and the filtrate was evaporated to dryness in vacuo. The residue was triturated with two ml. of methanol and filtered. The filtrate was diluted with 100 ml. of acetone and the solid product that separated was removed by filtration and dried; yield, 184 mg.

EXAMPLE 11

Preparation of β-phenylethyl-BM123γ

To a solution of 200 mg of BM123γ in 15 ml. of water and 25 ml. of acetonitrile was added a solution of 2 ml. of phenylacetaldehyde in 4 ml. of ethanol. To this was added 103 mg. of sodium cyanoborohydride. The reaction mixture was stirred at room temperature for 30 minutes during which time the pH of the mixture was maintained at 7 with 0.2N hydrochloric acid. The reaction mixture was then filtered and the filtrate was evaporated to dryness in vacuo. The residue was triturated with two ml. of methanol and filtered. The filtrate was diluted with 100 ml. of acetone and the product that separated was removed by filtration and dried; yield, 180 mg.

EXAMPLE 12

Preparation of 1,3,3-trimethylbutyl-BM123γ

To a solution of 200 mg. of BM123γ hydrochloride in 50 ml. of methanol was added 3 ml. of 4,4-dimethyl-2-pentanone and 106 mg. of sodium cyanoborohydride. The reaction solution was maintained at pH 7 by the dropwise addition of methanolic hydrogen chloride. The reaction was stirred at room temperature for 18 hours and filtered. The filtrate was evaporated to dryness in vacuo. The residue was dissolved in 3 ml. of methanol, diluted with 50 ml. of acetone and filtered, yield 125 mg.

EXAMPLE 13

Preparation of 1-methylphenethyl-BM123γ

To a solution of 200 mg. of BM123γ in 50 ml. of methanol was added 5 ml. of phenylacetone. To this solution was added 170 mg. of sodium cyanoborohydride and the reaction mixture stirred at room temperature for 3 and a half hours. During this time the pH of the reaction mixture was maintained at 7.0 with methanol saturated with hydrogen chloride gas. Reaction mixture was concentrated to about 5 ml. volume, diluted with two ml. of methanol, and filtered. Filtrate was poured into 100 ml. of acetone and the solid product that separated was removed by filtration and dried; yield, 233 mg.

EXAMPLE 14

Preparation of 1-methylnonyl-BM123γ

Sodium cyanoborohydride (100 mg.) was added to a solution of BM123γ (200 mg.) and 2-decanone (1 ml.) in 40 ml. of methanol. The pH of the solution was adjusted to 7.0 and maintained at 7.0 ± 0.2 by the addition of 0.1N methanolic hydrogen chloride as necessary. After 19.5 hours the reaction mixture was filtered and the filtrate was concentrated in vacuo at 35° C. The residue was slurried in 5 ml. of methanol and filtered. The filtrate was added to 50 ml. of acetone. The off white solid which precipitated was collected by filtration, washed with acetone, and dried in vacuo. The yield of crude 1-methylnonyl-BM123γ was 167 mg.

EXAMPLE 15

Preparation of 1,3-dimethylbutyl-BM123γ

To a solution of 210 mg. of BM123γ in 50 ml. of methanol was added 5 ml. of methyl isobutyl ketone. To this solution was added 166 mg. of sodium cyanoborohydride and the reaction mixture strired at room temperature for five hours. During this time the pH of the reaction mixture was maintained at 7.0 with methanol saturated with hydrogen chloride gas. Reaction mixture was evaporated to dryness, in vacuo. The residue was triturated with two ml. of methanol and filtered. The filtrate was diluted with 100 ml. of acetone and the solid product that separated was removed by filtration and dried; yield, 210 mg.

EXAMPLE 16

Preparation of 2-norbornyl-BM123γ

Sodium cyanoborohydride (100 mg.) was added to a solution of BM123γ (200 mg.) and 2-norbornanone (400 mg.) in 40 ml. of methanol. The pH of the solution was adjusted to 7.0 with 0.1N methanolic hydrogen chloride. The pH was maintained at 7.0 ± 0.2 by the addition of 0.1N hydrogen chloride as necessary. After 21.5 hours the reaction mixture was filtered and the filtrate was concentrated in vacuo at 35° C. The residue was slurried in 5 ml of methanol and filtered. The filtrate was added to 50 ml. of acetone. The off white solid which precipitated was collected by filtration, washed with acetone and dried in vacuo. The yield of crude 2-norbornyl-BM123γ was 175 mg.

EXAMPLE 17

Preparation of isopropyl-BM123γ$_1$

A mixture of 50 mg. of BM123γ$_1$, 5 ml. of acetone and 60 mg. of sodium cyanoborohydride in 35 ml. of methanol was stirred at room temperature for 40 minutes. The pH of the solution was maintained at 7 by the dropwise addition of a methanolic hydrogen chloride solution. The mixture was evaporated to dryness in vacuo. The residue was triturated with 5 ml. of methanol and the resulting solution was diluted with 50 ml. of acetone; yield, 49 mg.

EXAMPLE 18

Preparation of isopropyl-BM123γ$_2$

A mixture of 41 mg. of BM123γ$_2$, 5 ml of acetone and 50 mg. of sodium cyanoborohydride in 35 ml. of methanol was stirred at room temperature for 40 minutes. The pH of the solution was maintained at 7 by the dropwise addition of a methanolic hydrogen chloride solution (saturated). The mixture was filtered and evaporated to dryness in vacuo. The residue was triturated with 5 ml. of methanol and the resulting solution was diluted with 50 ml. of acetone; yield, 46 mg.

EXAMPLE 19

Preparation of 1-methyl-2-phenyl-ethyl-BM123γ$_2$

A mixture of 200 mg. of BM123γ$_2$, 5 ml of phenylacetone and 170 mg. of sodium cyanoborohydride in 50 ml. of methanol was stirred at room temperature for 3 hours and 45 minutes. During this time the pH of the reaction mixture was maintained at 7 with dropwise addition of a methanolic hydrogen chloride solution (saturated). The mixture was evaporated to dryness in vacuo. The residue was triturated with 5 ml. of methanol and the resulting methanol solution was diluted with approximately 50 ml. of acetone; yield 233 mg.

EXAMPLE 20

Preparation of (2-ethylcyclopentyl) BM123γ

A solution of 200 mg. of BM123γ, 3 ml. of 2-ethylcyclopentanone and 101 mg. of sodium cyanoborohydride in 50 ml. of methyl alcohol was stored at room temperature for 18 hours. During this time the pH of the solution was maintained at 7 with the addition of a saturated solution of hydrogen chloride in methanol. The reaction mixture was evaporated to dryness. The residue was triturated with 3 ml. of methanol, filtered and the filtrate was diluted with 40 ml. of acetone, yield, 157 mg.

EXAMPLE 21

Preparation of 3,5-dimethylcyclohexyl BM123γ

A solution of 200 mg. of BM123γ, 5 ml. of 3,5-dimethylcyclohexanone and 200 mg. of sodium cyanoborohydride in 50 ml. of methanol was stored at room temperature for 1 hour. During this time the pH of the solution was maintained at 7 with the addition of a saturated solution of hydrogen chloride in methanol. The reaction was triturated with 3 ml. of methanol, filtered and the filtrate was diluted with 40 ml. of acetone, yield 200 mg.

EXAMPLE 22

Preparation of 2,4-dimethylcyclopentyl BM123γ

A solution of 206 mg. of BM123γ, 3 ml. of 2,4-dimethylcyclopentanone and 104 mg. of sodium cyanoborohydride in 50 ml. of methanol was stored at room temperature for 6 hours. During this time the pH of the solution was maintained at 7 with the addition of a saturated solution of hydrogen chloride in methanol. The reaction was triturated with 3 ml. of methanol, filtered and the filtrate was diluted with 40 ml. of acetone, yield 101 mg.

EXAMPLE 23

Preparation of 2-ethylcyclohexyl BM123γ

A solution of 200 mg. of BM123γ, 5 of 2-ethylcyclohexanone and 213 mg. of sodium cyanoborohydride in 50 ml. of methanol was stored at room temperature for 3 hours. During this time the pH of the solution was maintained at 7 with the addition of a saturated solution of hydrogen chloride in methanol. The reaction was triturated with 3 ml. of methanol, filtered and the filtrate was diluted with 40 ml. of acetone, yield 200 mg.

EXAMPLE 24

Preparation of 3-methylcyclohexyl BM123γ

A solution of 200 mg. of BM123γ, 1.5 ml. of 3-methylcyclohexanone and 200 mg. of sodium cyanoborohydride in 50 ml. of methanol was stored at room temperature for 2 hours. During this time the pH of the solution was maintained at 7 with the addition of a saturated solution of hydrogen chloride in methanol. The reaction was triturated with 3 ml. of methanol, filtered and the filtrate was diluted with 40 ml. of acetone, yield 200 mg.

EXAMPLE 25

Preparation of 2,4,4-trimethylcyclopentyl BM123γ

A solution of 200 mg. of BM123γ, 5 ml. of 2,4,4-trimethylcyclopentanone and 179 mg. of sodium cyanoborohydride in 50 ml. of methanol was stored at room temperature for 24 hours. During this time the pH of the solution was maintained at 7 with the addition of a saturated solution of hydrogen chloride in methanol. The reaction was triturated with 3 ml. of methanol, filtered and the filtrate was diluted with 40 ml. of acetone, yield 176 mg.

EXAMPLE 26

Preparation of 2-propylcyclohexyl BM123γ

A solution of 200 mg. of BM123γ, 3 ml. of 2-propylcyclohexanone and 157 mg. of sodium cyanoborohydride in 50 ml. of methanol was stored at room temperature for 4 hours. During this time the pH of the solution was maintained at 7 with the addition of a saturated solution of hydrogen chloride in methanol. The reaction was triturated with 3 ml. of methanol, filtered an the filtrate was diluted with 40 ml. of acetone, yield 75 mg.

EXAMPLE 27

Preparation of 2-methylcyclopentyl BM123γ

A solution of 211 mg. of BM123γ, 3 ml. of 2-methylcyclopentanone and 98 mg. of sodium cyanoborohydride in 50 ml. of methanol as stored at room temperature for 3.5 hours. During this time the pH of the solution was maintained at 7 with the addition of a saturated solution of hydrogen chloride in methanol. The reaction was triturated with 3 ml. of methanol, filtered and the filtrate was diluted with 40 ml. of acetone, yield 157 mg.

We claim:

1. A compound selected from the group consisting of those of the formulae:

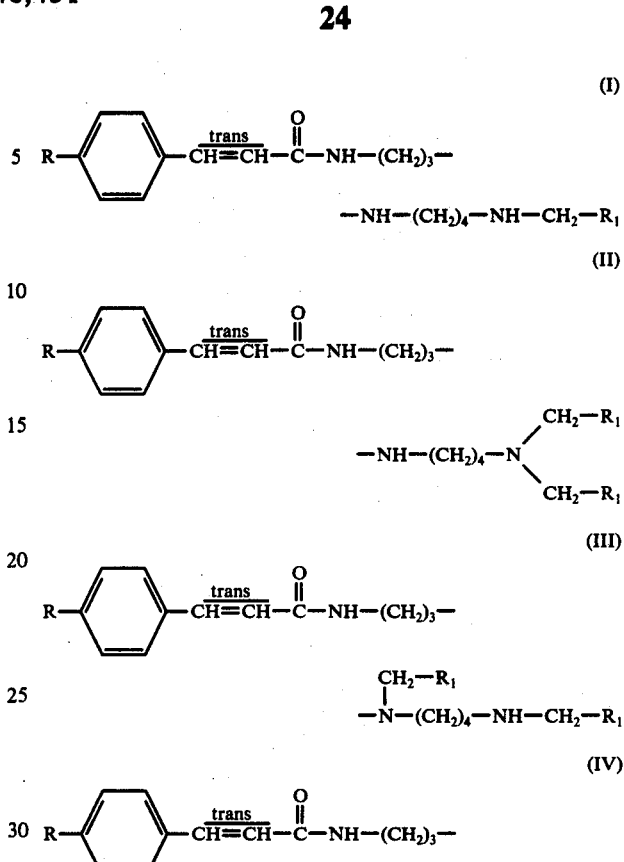

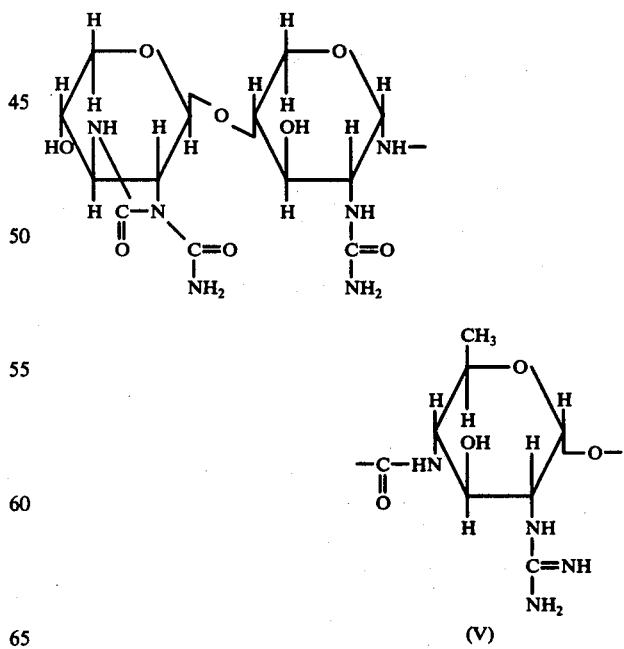

wherein R is a moiety selected from the group consisting of those of the formulae:

and

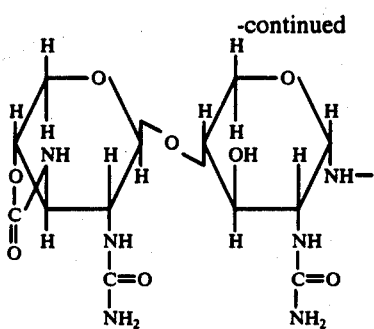

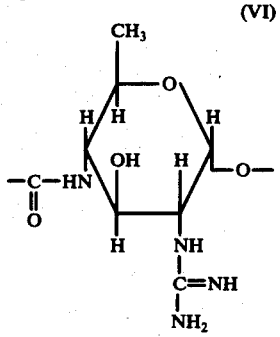

(VI)

$R_1$ is selected from the group consisting of hydrogen, lower alkyl, halo substituted lower alkyl, lower alkenyl, phenyl, acetamidophenyl, nitrophenyl, mercaptophenyl, anisyl, tolyl, phenyl lower alkyl, 2-furyl, methyl substituted 2-furyl, 2thienyl, methyl substituted 2-thienyl, 2-pyrryl, methyl substituted 2-pyrryl, 2-pyridyl and 2-quinolyl; and the pharmacologically acceptable acid-addition salts thereof.

2. A mixture consisting essentially of a compound according to claim 1, formula (I) thereof, wherein R is moiety (V) and a compound according to claim 1, formula (I) thereof, wherein R is moiety (VI).

3. A mxiture consisting essentially of a compound according to claim 1, formula (II) thereof, wherein R is moiety (V) and a compound according to claim 1, formula (II) thereof, wherein R is moiety (VI).

4. A mixture consisting essentially of a compound according to claim 1, formula (III) thereof, wherein R is moiety (V) and a compound according to claim 1, formula (III) thereof, wherein R is moiety (VI).

5. A mixture consisting essentially of a compound according to claim 1, formula (IV) thereof, wherein R is moiety (V) and a compound according to claim 1, formula (IV) thereof, wherein R is moiety (VI).

6. The mixture in accordance with claim 2 wherein $R_1$ is hydrogen.

7. The mixture in accordance with claim 2 wherein $R_1$ is methyl.

8. The mixture in accordance with claim 2 wherein $R_1$ is benzyl.

9. The mixture in accordance with claim 2 wherein $R_1$ is 1,1-dimethylpropyl.

10. The mixture in accordance with claim 2 wherein $R_1$ is trans-1-methylpropen-1-yl.

11. The mixture in accordance with claim 3 wherein $R_1$ is hydrogen.

12. The mixture in accordance with claim 3 wherein $R_1$ is methyl.

13. The mixture in accordance with claim 4 wherein $R_1$ is hydrogen.

14. The mixture in accordance with claim 4 wherein $R_1$ is methyl.

15. The mixture in accordance with claim 5 wherein $R_1$ is hydrogen.

16. The mixture in accordance with claim 5 wherein $R_1$ is methyl.

17. A compound selected from the group consisting of those of the formula:

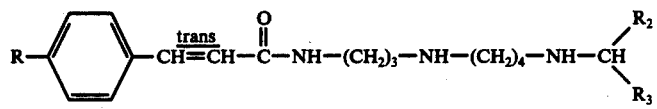

wherein R is a moiety selected from the group consisting of those of the formulae:

(A)

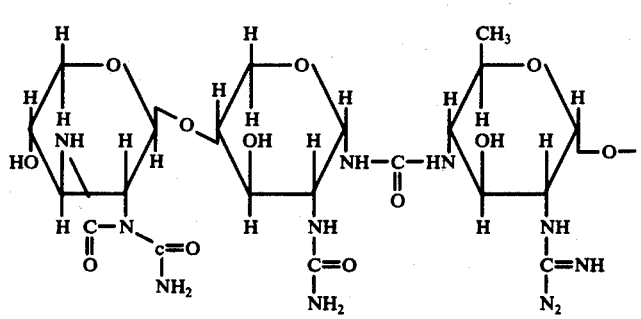

and
(B)

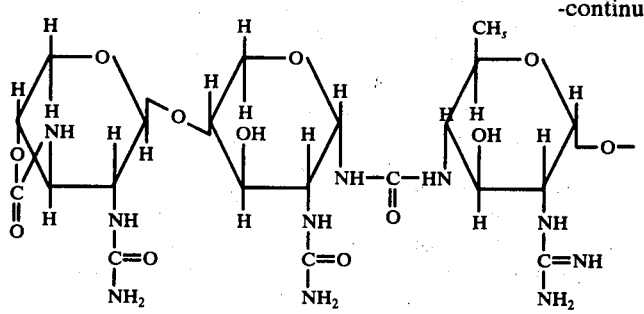

$R_2$ is selected from the group conisting of lower alkyl, halo substituted lower alkyl and phenyl lower alkyl; $R_3$ is selected from the group consisting of lower alkyl, halo substituted lower alkyl, lower alkenyl, lower cycloalkyl, phenyl, acetamidophenyl, nitrophenyl, mercaptophenyl, anisyl, tolyl, phenyl lower alkyl, acetamidophenyl lower alkyl, nitrophenyl lower alkyl, mercaptophenyl lower alkyl, anisyl lower alkyl and tolyl lower alkyl; and $R_2$ and $R_3$ taken together with the associated methylidyne group is cyclopentyl, mono-lower alkyl substituted cyclopentyl, di-lower alkyl substituted cyclopentyl, tri-lower alkyl substituted cyclopentyl, cyclohexyl, mono-lower alkyl substituted cyclohexyl, di-lower alkyl substituted cyclohexyl or tri-lower alkyl substituted cyclohexyl; and the pharmacologically acceptable acid-addition salts thereof.

18. A mixture consisting essentially of a compound according to claim 17 wherein R is moiety (A) and a compound according to claim 17 wherein R is moiety (B).

19. The compound according to claim 17 wherein R is moiety (A), $R_2$ is methyl, and $R_3$ is methyl.

20. The compound according to claim 17 wherein R is moiety (B), $R_2$ is methyl, and $R_3$ is methyl.

21. The mixture in accordance with claim 18 wherein $R_2$ is methyl and $R_3$ is methyl.

22. The compound according to claim 17 wherein R is moiety (A), $R_2$ is ethyl, and $R_3$ is methyl.

23. The compound according to claim 17 wherein R is moiety (B), $R_2$ is ethyl, and $R_3$ is methyl.

24. The mixture in accordance with claim 18 wherein $R_2$ is ethyl and $R_3$ is methyl.

25. The compound according to claim 17 wherein R is moiety (A), $R_2$ is ethyl, and $R_3$ is ethyl.

26. The compound according to claim 17 wherein R is moiety (B) $R_2$ is ethyl, and $R_3$ is ethyl.

27. The mixture in accordance with claim 18, wherein $R_2$ is ethyl and $R_3$ is ethyl.

28. The mixture in accordance with claim 18 wherein $R_2$ is methyl and $R_3$ is n-propyl.

29. The mixture in accordance with claim 18 wherein $R_2$ is methyl and $R_3$ is benzyl.

30. The mixture in accordance with claim 18 wherein $R_2$ is methyl and $R_3$ is 2-methylpropyl.

31. The mixture in accordance with claim 18 wherein $R_2$ is methyl and $R_3$ is isopropyl.

32. The mixture in accordance with claim 18 wherein $R_2$ is methyl and $R_3$ is 2,2-dimethylpropyl.

33. The mixture in accordance with claim 18 wherein $R_2$ is ethyl and $R_3$ is butyl.

34. The mixture in accordance with claim 18 wherein $R_2$ is methyl and $R_3$ is 1-methylpropyl.

35. The mixture in accordance with claim 18 wherein $R_2$ is methyl and $R_3$ is 2-phenylethyl.

36. The mixture in accordance with claim 18 wherein $R_2$ is methyl and $R_3$ is 3-methylbutyl.

* * * * *